United States Patent [19]

Deane et al.

[11] Patent Number: 4,708,717
[45] Date of Patent: Nov. 24, 1987

[54] SUCTION-IRRIGATION APPARATUS

[75] Inventors: Graham Deane, Ascot; Barry O. Weightman, Cobham, both of England

[73] Assignee: National Research Development Corporation, London, England

[21] Appl. No.: 832,768

[22] Filed: Feb. 25, 1986

[30] Foreign Application Priority Data

Feb. 26, 1985 [GB] United Kingdom ................. 8504906

[51] Int. Cl.⁴ ............................................. A61M 1/00
[52] U.S. Cl. ........................................ 604/35; 604/43;
604/266; 239/42
[58] Field of Search ................... 604/35, 266, 902, 43;
239/112, 106, 119, 124, 125, 110, 569

[56] References Cited

U.S. PATENT DOCUMENTS

| 3,963,028 | 6/1976 | Cooley et al. | 604/902 X |
| 4,022,218 | 5/1977 | Riddich | 604/902 X |
| 4,244,494 | 1/1981 | Colgate et al. | 239/112 X |
| 4,397,604 | 8/1983 | Haug et al. | 604/35 X |
| 4,518,398 | 5/1985 | Wuchinich | 604/35 X |
| 4,540,406 | 9/1985 | Miles | 604/902 X |

FOREIGN PATENT DOCUMENTS

| 1470153 | 4/1977 | United Kingdom . |
| 2058576A | 4/1981 | United Kingdom . |
| 2117244A | 3/1982 | United Kingdom . |
| 2117245A | 10/1983 | United Kingdom . |
| 939112 | 1/1982 | U.S.S.R. | 239/112 |

OTHER PUBLICATIONS

U.K. Official Search Report dated 11 Apr. 1986.

Primary Examiner—Andres Kashnikow
Assistant Examiner—Kevin Patrick Weldon
Attorney, Agent, or Firm—Cushman, Darby & Cushman

[57] ABSTRACT

Suction-irrigation apparatus for medical use in relation to wound and surgical sites comprises a probe projecting from a handpiece which also carries a valve, there being a through-conduit opening at the probe tip for suction, a first irrigation conduit opening at the tip, and a second irrigation conduit communicating with the suction conduit adjacent the tip, and with the valve normally operable to control the flow of fluid through the irrigation conduits. Preferably the valve operation has a normal position with both irrigation conduits closed, a fully operated position with only the first such conduit open, and a partially operated intermediate position with only the second such conduit open.

7 Claims, 1 Drawing Figure

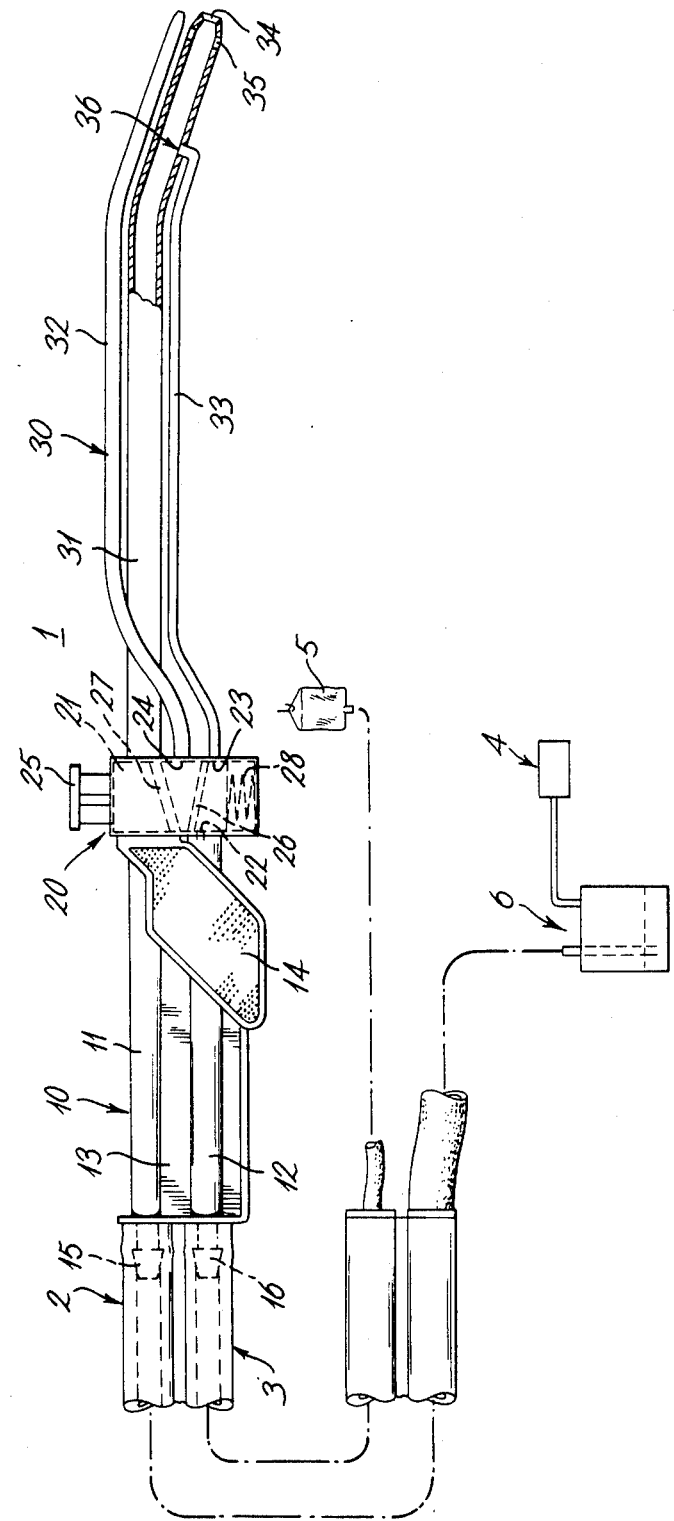

SUCTION-IRRIGATION APPARATUS

This invention concerns suction-irrigation apparatus and more particularly such apparatus for medical use in the cleaning or treatment of wound and surgical sites.

It is often necessary to remove foreign matter and/or debris from a wound or surgical site and this can be accomplished by irrigating the site with a fluid to suspend therein the material to be removed and sucking away the fluid and suspended material by use of an appropriate probe. One of the major difficulties with such procedure is that the probe and its associated suction line frequently become blocked by accumulation of solid material.

This last difficulty is particularly prevalent in orthopaedic surgery, in which suction-irrigation is commonly deployed for the removal of excised bone and other matter, because the surgical procedures often give rise to large amounts of bone chips of varying size which cause blockages. Such blockages cause delay in the preocedure while clearance is effected or the probe and/or its line are replaced.

An object of the present invention is to provide suction-irrigation which is less prone to such blockage.

According to the present invention there is provided suction-irrigation apparatus comprising: a handpiece; a probe projecting from said handpiece to terminate in an operative tip; a suction conduit extending through said apparatus to open at one end from said handpiece for connection to a source of suction and at the other end at said operative tip; first and second irrigation conduits each extending through said apparatus to open at one end from said handpiece for connection to a supply of irrigating fluid, said first conduit opening at its other end at said tip, and said second conduit being communicated at its other end with said suction conduit adjacent said tip; and valve means carried by said handpiece and manually operable to control the supply of irrigating fluid to said first and second conduit other ends.

In use of this apparatus, irrigation fluid can be supplied directly into the suction conduit so as periodically to flush out the latter with clean fluid thereby preventing accumulation of solid matter and reducing the risk of blockage.

The invention and preferred features thereof will now be clarified and described, by way of example, with reference to the accompanying drawing, the single FIGURE of which shows one embodiment of the invention in a schematic side elevation.

The drawing in fact shows a suction-irrigation apparatus denoted generally at 1 and according to the invention, connected via flexible hose lines 2 and 3 respectively to a suction source 4 and a source 5 of irrigaiton fluid for supply to the apparatus under pressure. A suction source is commonly available in an operating theatre as a permanent facility, usually by way of a valved hose terminal in the theatre connected to a remote pump or other primary suction source. Whether this is the case or an independent primary source is used, it will normally be appropriate to connect a collection vessel to receive removed fluid and material between the primary source and suction line and such a vessel is denoted at 6. The fluid source is conveniently a bag of saline solution located in an elevated position to provide a pressurised fluid supply by gravitational action, but alternative arrangements can be employed involving a pump and fluid reservoir.

The apparatus comprises an overall elongated structure formed by a serial connection of a handpiece 10, a valve 20 and a probe 30.

The handpiece 10 is a one-piece plastics moulding having two parallel tubular formations 11 and 12 separated from one another by a land 13. Towards one end the moulding incorporates a formation 14 which projects in a transversely inclined manner across and beyond the tubular formations to facilitate one-handed gripping with the fingers passing around and below the handpiece and the thumb passing forwardly above the handpiece. At its other end the tubular formations 11 and 12 terminate in connectors 15 and 16 respectively to receive the hose lines 2 and 3 in communication with the bores of such formations.

The valve 20 has a valve body 21 connected with the handpiece end adjacent the grip formation 14. The body 21 has an inlet port 22 communicated with the bore of tubular formation 12, and has two mutually spaced outlet ports 23 and 24. A valve member 25 formed with two transverse bores 26 and 27 is sealably and slidably located in the body 21. The valve member projects from the valve body under the action of a bias spring 28, in opposite manner to the grip formation projection from the handpiece, to suit operation by a user's thumb. In its normal biassed position the valve member bores are displaced from the inlet port in the valve body. Upon operation of the valve member to slide within the body the bore 26 is first communicated at its ends with the inlet port and the outlet port 23, and thereafter with continued operational movement the bore 27 is communicated at its ends with the inlet port and outlet port 24 while bore 26 is discommunicated.

The probe 30 comprises three tubes 31, 32 and 33 extending in generally parallel manner from the handpiece and valve.

The tube 31 is communicated at one end directly with the bore of the tubular formation 11 of the handpiece and forms a suction conduit which is permanently open. At its other end the bore of tube 31 opens longitudinally by way of an aperture 34 and this bore is also transversely opened adjacent such end by way of a plurality of apertures 35 around the tube. The apertures 34 and 35 are each of smaller cross-sectional dimensions than the bore of tube 31.

The tube 32 is communicated at one end with the outlet port 24 of the valve 20, and so with the bore of tubular formation 12 of the handpiece when the valve is appropriately operated, to form a first irrigation conduit. At its other end the tube 32 is open and extends to a location level with tube 31 but to one side thereof in the same sense as the valve member projection from its body.

The tube 33 is communicated at one end with the outlet port 23 of the valve 20, and so with the bore of tubular formation 12 of the handpiece when the valve is appropriately operated, to form a second irrigation conduit. At its other end the tube is connected with a port 36 in the tube 32 to intercommunicate the two tubes, the port 36 being adjacent to the aperture 34 but further therefrom than the apertures 35. Also the tube 33 extends along one side of tube 32 to the port 36 in opposite manner to tube 31 over much of its length.

The general operation of the illustrated apparatus is largely evident from the above description. Thus, the apparatus is gripped by the handpiece to apply the probe to a site so that fluid and free solids are sucked away through the apertures 34 and 35 of tube 31. When appropriate, the user can fully operate the valve so that fluid is supplied by way of the tube 32 to irrigate the site. It will be appreciated that when fully operating the valve, or releasing the valve from such operation, it necessarily passes through a position in which fluid is supplied to the tube 33. This fluid is sucked back along the suction conduit, and its associated line, and will act to flush out any build-up of solid matter and so reduce the risk of blockage. The repetitive irrigation which is commonly appropriate in the use of suction-irrigation will normally suffice, with the automatic flushing just described, to maintain the suction conduit and its line free from blockage. However, a user can of course partially operate the valve to effect additional or sustained flushing action if desired, as may be appropriate in operations involving large amounts of debris., It will be noted that the suction tube apertues 34 and 35 are smaller than the tube bore: this is an additional preventive measure against blockage because any discrete element of solid material entering the bore will be inherently capable of free passage through the bore. Also, as a further blockage preventive measure, it is preferred that the suction conduit has no restrictions or convergent tapers from the aperture 34 back to hose connector 15.

Lastly, it will be appreciated that although the drawing represents a presently preferred form of the invention, variation is possible within the scope of the appended claims. For example, as shown, the probe is angled downwardly towards its tip, with the first and second irrigation conduit tubes respectively above and below the suction conduit tube, and the orientation of this configuration is controllable by reference to the valve positioning and that of the user's thumb above the valve. However the use of such a configuration and referencing is by no means critical and can be varied if desired. Similarly, while preferable as a structurally simplified arrangement giving automatic flushing in normal usage, the valve arrangement can be varied. A different operational sequence can be provided, or even separate valves. Also a suction conduit valve can be provided, although an equivalent valve function can be provided in the suction line.

We claim:

1. Suction-irrigation apparatus comprising: a handpiece; a probe projecting from said handpiece to terminate in an opposite tip; a suction conduit extending through said apparatus to open at one end from said handpiece for connection to a source of suction and at the other end at said operative tip; first and second irrigation conduits each extending through said apparatus to open at one end from said handpiece for connection to a supply of irrigating fluid, said first conduit opening at its other end at said tip, and said second conduit being communicated at its other end with said suction conduit adjacent said tip; and valve means carried by said handpiece to control the supply of irrigating fluid to said first and second conduit other ends, said valve means including a manually operable valve member selectively movable between first, second and third operable positions in which, respectively, both and first and second conduits are closed, said first conduit is closed while said second conduit is open, and said first conduit is open while said second conduit is closed.

2. Apparatus according to claim 1 wherein said valve member is movable between said first and third positions by way of said second position.

3. Apparatus according to claim 2 wherein said valve member is biassed normally to adopt said first position.

4. Apparatus according to claim 1 wherein said first and second conduits are partially combined in a common conduit portion extending through said handpiece to open therefrom for connection to a common fluid source.

5. Apparatus according to claim 1 wherein said valve member projects transversely from said apparatus on one side thereof relative to said probe said first conduit extends along said suction conduit on said one side of the latter, and said second conduit extends along said suction conduit on the opposite side thereof from said first conduit.

6. Apparatus according to claim 1 wherein said suction conduit opens at its other end by way of a longitudinal end aperture and a plurality of transverse apertures adjacent thereto, said transverse apertures being longitudinally closer to said end aperture than is said second conduit.

7. Apparatus according to claim 1 wherein said suction conduit opens at its other end by way of at least one aperture of lesser internal cross-sectional dimensions than said suction conduit.

* * * * *